United States Patent
Jang

(10) Patent No.: US 8,557,184 B2
(45) Date of Patent: Oct. 15, 2013

(54) DEVICES AND METHODS FOR MEASURING THE ACIDITY OF AIRBORNE MATTER USING UV-VISIBLE SPECTROMETRY

(75) Inventor: Myoseon Jang, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 380 days.

(21) Appl. No.: 12/742,701

(22) PCT Filed: Dec. 23, 2008

(86) PCT No.: PCT/US2008/088161
§ 371 (c)(1),
(2), (4) Date: Jul. 19, 2010

(87) PCT Pub. No.: WO2009/088773
PCT Pub. Date: Jul. 16, 2009

(65) Prior Publication Data
US 2010/0279427 A1    Nov. 4, 2010

Related U.S. Application Data

(60) Provisional application No. 61/020,051, filed on Jan. 9, 2008.

(51) Int. Cl.
*G01J 1/48* (2006.01)
(52) U.S. Cl.
USPC ............... 422/86; 422/50; 422/65; 422/67; 422/68.1; 422/83; 422/88
(58) Field of Classification Search
None
See application file for complete search history.

(56) References Cited

U.S. PATENT DOCUMENTS

| | | |
|---|---|---|
| 6,512,577 B1 | 1/2003 | Ozanich |
| 6,885,003 B1 | 4/2005 | Dubernet |
| 2006/0087656 A1 | 4/2006 | Barford et al. |

OTHER PUBLICATIONS

Houk, V. S. et al. Mutagenicity of teflon-coated glass fiber filters: a potential problem and solutions, 1987, Environmental Science Technology, vol. 21(9), pp. 917-920.*
Chasteen, C.C., Automated measurement of aerosol acidity, 1996, Thesis in Chemistry, Master of Science, Texas Tech University.*
Cao. et al. "Effects of particle acidity and UV light on secondary organic aerosol formation from oxidation of aromatics in the absence of NOx," *Atmospheric Environment*, Nov. 2007, pp. 7603-7613, vol. 41.
Czoschke et al. "Acidity effects on the formation of α-pinene ozone SOA in the presence of inorganic seed" *Atmospheric Environment*, 2006, pp. 4370-4380, vol. 40.
Jang et al. "Atmospheric secondary aerosol formation of heterogeneous reactions of aldehydes in the presence of a sulfuric acid aerosol catalyst" *Environ. Sci. Technol.*, 2001, pp. 4758-4766, vol. 35.
Jang, et al. "SOA formation from partitioning and heterogeneous reactions: Model study in the presence of inorganic species" *Environ. Sci. Technol.*, 2006, pp. 3013-3022, vol. 40.
Liggio et al. "Heterogeneous reactions of glyoxal on particulate matter: Identification of acetals and sulfate esters" *Environ. Sci. Tecnhol.*, 2005, pp. 1532-1541, vol. 39.

(Continued)

*Primary Examiner* — Robert Xu
(74) *Attorney, Agent, or Firm* — Saliwanchik, Lloyd & Eisenschenk

(57) ABSTRACT

Devices and methods for measuring the acidity of airborne matter are provided. A filter can be impregnated with an indicator dye which changes color in response to changes in acidity. After the sample passes through the filter, the filter can be analyzed using UV-visible spectrometry.

4 Claims, 8 Drawing Sheets

(56) References Cited

OTHER PUBLICATIONS

McMurry, P. H. "Gas and aerosol wall losses in Teflon film smog chambers" *Environ. Sci. Technol.*, 1985, pp. 1176-1182, vol. 19.

Nakano and Yamamoto "Development of a monitoring tape for hydrogen chloride gas using metanil yellow" *Analyst*, 1993, pp. 1539-1542, vol. 118.

Northcross and Jang "Heterogeneous SOA yield from ozonolysis of monoterpenes in the presence of inorganic acid" *Atmospheric Environment*, 2007, pp. 1483-1493, vol. 41.

Surratt et al. "Evidence for organosulfates in secondary organic aerosol" *Environ. Sci. Technol.*, 2007, pp. 517-527, vol. 41.

* cited by examiner (A) H$_2$SO$_4$ reaction with aldehydes (B) H$_2$SO$_4$ reaction with a dimer of aldehydes (C) H$_2$SO$_4$ reaction with aldol condensation products (D) H$_2$SO$_4$ reaction with bicarbonyl (E) H$_2$SO$_4$ reaction with oligomers

DEVICES AND METHODS FOR MEASURING THE ACIDITY OF AIRBORNE MATTER USING UV-VISIBLE SPECTROMETRY

CROSS REFERENCE TO A RELATED APPLICATION

This application is a National Stage Application of International Application Number PCT/US2008/088161, filed Dec. 23, 2008; which claims priority to U.S. Provisional Application No. 61/020,051, filed Jan. 9, 2008; both of which are incorporated herein by reference in their entirety.

GOVERNMENT SUPPORT

The subject matter of this application has been supported by research grants from the National Science Foundation under grant numbers ATM-0703914 and nano-NER-0508247. Accordingly, the government has certain rights in this invention.

BACKGROUND OF THE INVENTION

The ability to determine the acidity of airborne matter is very important. The presence of certain acidic compounds in the air, such as sulfuric acid, can have adverse health effects. In addition, the measure of aerosol acidity has important implications for public health and workplace conditions. For example, research has shown that there may be a strong correlation between aerosol hydronium concentration and many problems associated with air pollution. The detection of acidic pollutants is also very critical in the many working environments such as the mining industry, fertilizer manufacturing, air plumes from waste landfills, coal power plants, petroleum refineries, and offices located in polluted city areas.

Additionally, accurate measurements of the acidity of the air can help in a wide range of other experiments and studies. For example, studies on secondary organic aerosols (SOAs) are largely dependent on measuring the acidity of airborne particulate matter over time.

In general, ambient particulate matter consists of inorganic and organic constituents. The inorganic matter can include sulfates, ammonium, nitrates, sea salts, crusts, and metal oxides. The organic species consists of elemental carbon and organic carbon. A significant class of organic carbon present in ambient particulate matter is secondary organic aerosol (SOA), which can make up about 20% to about 90% of the ambient organic carbon, depending on location and season.

Currently, evaluation of the effects of particle acidity on ambient SOA is limited by existing analytical methods using a pH meter or ion chromatography (EPA Method IO-4.2. *Determination of the strong acidity of atmospheric fine particles (<2.5 micrometer)*, U.S. EPA, Center for Environmental Research Information, Office of Research and Development, 1999). Such existing methods focus on measurement of major inorganic ions such as sulfate, nitrate, and ammonium with the assumption that the consumption of inorganic acids is dominated by ammonia titration. Additionally, these existing methods require water extraction and are inefficient for monitoring changes in aerosol acidity over short periods of time since measurement of the acidity is not a short process.

Furthermore, existing methods for measuring acidity of airborne particulate matter may be inaccurate in many cases. For example, such methods may incorrectly estimate proton concentration in aerosol by neglecting the formation of organic sulfates in SOA.

Thus, there exists a need in the art for an improved device and method of measuring the acidity of airborne matter.

BRIEF SUMMARY OF THE INVENTION

The present invention provides devices and methods for measuring the acidity of airborne matter. The acidity can be measured quickly, cleanly, and without the need for solvent extraction.

In one embodiment, a device for measuring the acidity of airborne matter can include a detector chamber with a filter. The filter can be impregnated with an indicator dye which changes color in response to changes in acidity. The indicator dye can be, for example, metanil yellow. After the sample passes through the filter, the filter can be analyzed using UV-visible spectrometry.

In another embodiment, a method for measuring the acidity of airborne matter can include passing an aerosol sample through a filter impregnated with an indicator dye. Then, the filter can be analyzed using UV-visible spectrometry. The filter can either be relocated to a spectrometer for analysis, or the spectrometer can be arranged in advance such that the filter can be analyzed in place after the sample passes through it.

Advantageously, the devices and methods of the present invention can be used to measure the acidity of airborne matter in a short period of time, such as from about 20 seconds to about 2 minutes. Additionally, the present invention can be environmentally friendly and does not require water extraction.

DETAILED DESCRIPTION OF THE INVENTION

The present invention provides novel devices and methods for measuring the acidity of airborne particulate matter. Advantageously, the devices and methods can measure the acidity of particulate matter very quickly and without the need for solvent extraction. Furthermore, the devices and methods of the present invention are completely or almost completely chemical-free and are therefore environmentally safe.

The devices and methods of the present invention utilize colorimetry and UV-visible spectrometry to determine the acidity of an aerosol sample. A filter for the sample can have an indicator dye applied to it so that the sample may cause color changes in the indicator dye. UV-visible spectrometry, such as reflectance UV-visible spectrometry, is used to monitor color changes on the filter.

Figure 1:
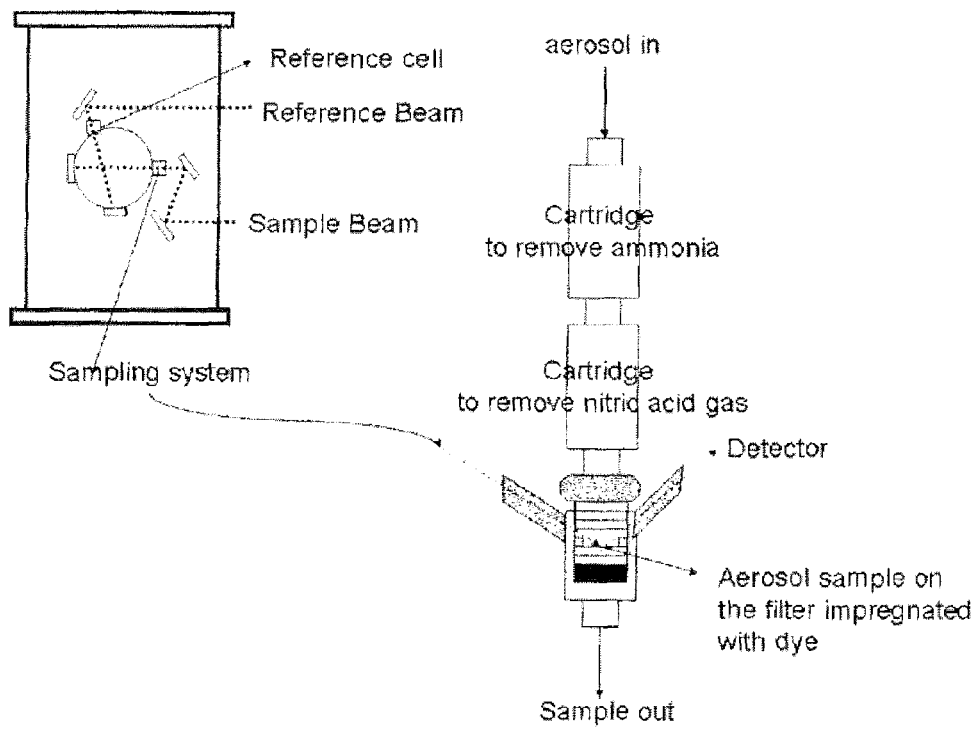
FIG. 1 shows a schematic view of a device for measuring the acidity of particulate matter according to an embodiment of the present invention.

Referring to FIG. 1, in one embodiment, a device to measure the acidity of airborne particulate matter can include means for accepting an aerosol sample and means for releasing the sample after it has been analyzed. The means for accepting and releasing the sample can be, for example, openings or holes that may be covered and uncovered. A cartridge to remove ammonia and a cartridge to remove nitric acid gas can also be included. The device can also have a detector chamber which can accept the aerosol sample after it has passed through the cartridges, and the detector chamber can include a filter through which the aerosol sample passes. In addition, the filter can be impregnated with an indicator dye that changes color depending on the composition of the aerosol sample.

Figure 2:
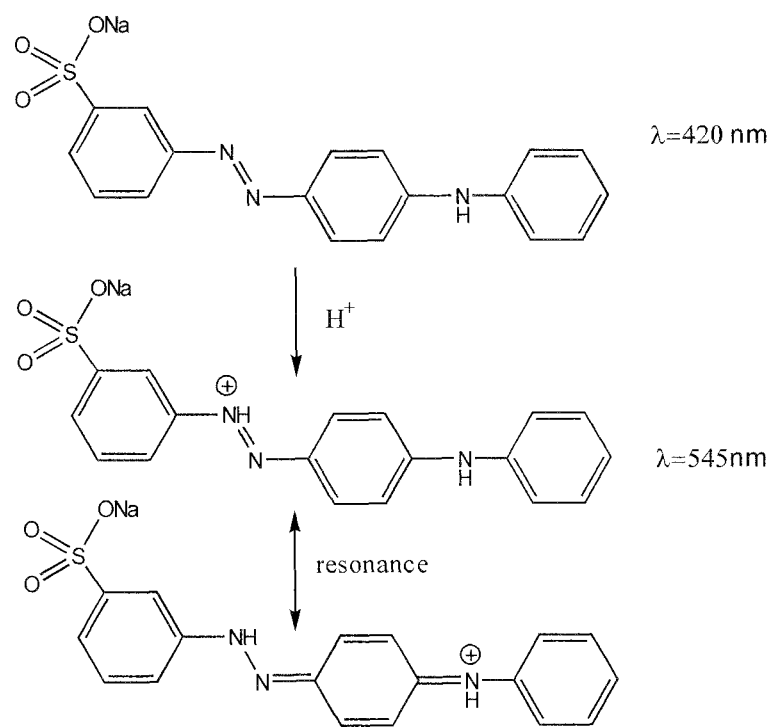
FIG. 2 shows molecular structures of metanil yellow and protonated metanil yellow.

The indicator dye can be any suitable dye known in the art, such as metanil yellow. Advantageously, metanil yellow has a dramatic color change between acid-base conjugate pairs, and it is sensitive to strong inorganic acids such as sulfuric acid, nitric acid, and ammonium hydrogen sulfate. Also, metanil yellow tends to be quite stable under natural light (Nakano et al., *Development of a Monitoring Tape for Hydrogen Chloride Gas Using Metanil Yellow, Analyst,* 1993, 1539: 1542). The molecular structures of metanil yellow and protonated metanil yellow are shown in FIG. 2. The transition interval of metanil yellow is pH 1.5 (red) to pH 2.7 (yellow) in aqueous solution. Furthermore, the UV-visible spectra of protonated metanil yellow can be shifted to a longer wavelength near 545 nm, which is unlikely to overlap with the UV-visible absorbance of atmospheric organics, which is usually less than 400 nm (Kiss et al., *Estimation of the Average Molecular Weight of Humic-like Substances Isolated from Fine Atmospheric Aerosol, Atmos. Environ.* 37, 2003, 3783:3794).

The filter can be made of any suitable material known in the art. In general, the filter material should be chosen such that the impact on the measurement of the acidity of the aerosol sample can be minimized. For example, the filter can be made of Teflon polymers and glass fibers, neither of which mix with particulate matter or affect the chemical properties of aerosols. Advantageously, the water uptake by a Teflon-impregnated filter is trivial, and the filter will not be significantly affected by a change in humidity.

In another embodiment, a method for measuring the acidity of airborne matter can include collecting an aerosol sample on a filer impregnated with an indicator dye and analyzing the filter using UV-visible spectrometry. The filter can be removed from the sampling area and moved to a separate spectrometer for analysis after the sample passes through it. Alternatively, a spectrometer can be positioned such that the filter can be analyzed in place after the sample passes through it.

The method for measuring the acidity of airborne matter according to the present invention can optionally include collecting an aerosol sample and releasing the sample after it has been analyzed. Additionally, ammonia and/or nitric acid gas can be removed from the sample using cartridges before the sample passes through the filter.

The indicator dye can be any suitable dye known in the art, such as metanil yellow. Advantageously, metanil yellow has a dramatic color change between acid-base conjugate pairs, and it is sensitive to strong inorganic acids such as sulfuric acid, nitric acid, and ammonium hydrogen sulfate. Also, metanil yellow tends to be quite stable under natural light (Nakano et al., 1993, supra). The molecular structures of metanil yellow and protonated metanil yellow are shown in FIG. 2. The transition interval of metanil yellow is pH 1.5 (red) to pH 2.7 (yellow) in aqueous solution. Furthermore, the UV-visible spectra of protonated metanil yellow can be shifted to a longer wavelength near 545 nm, which is unlikely to overlap with the UV-visible absorbance of atmospheric organics, which is usually less than 400 nm (Kiss et al., 2003, supra).

The indicator dye can be added in a low concentration to minimize its effect on the acidity of the system. For an indicator dye, the acid ionization constant (Ka) can be represented by Equation 1, where $[H^+]$ is the proton concentration, $[HIn^+]$ is the concentration of the acid form of the indicator dye, and $[In]$ is the concentration of the base form of the indicator dye.

$$K_a = [H^+][In]/[HIn^+] \quad (1)$$

For conventional aqueous titration, where the ratio $[In]/[HIn^+]$ is one, $[H^+] = K_a$ and $pH = pK_a$. This point would correspond to the color-change region of the indicator dye.

If $[H^+] = a$ before interaction between protons and indicator dye molecules, the $K_a$ after interaction can be represented by Equation 2.

$$K_a = \frac{(a - [HIn^+])[In]}{[HIn^+]} \quad (2)$$

In many embodiments of the present invention, the amount of indicator dye on the sampling area of the filter is on the order of about $10^{-11}$ moles (mol). The approximate level of protons which can be detectable by the present invention is on the order of about $10^{-10}$ mol. Thus, the proton concentration in an aerosol sample is not significantly impacted by the presence of the indicator dye and effectively becomes a constant in a given aerosol sample. Then, Equation 2 can be simplified into Equation 3.

$$a = K_a[HIn^+]/[In] \quad (3)$$

If $[In] = b$ before the interaction of protons with indicator dye molecules, the $K_a$ after interaction can be represented by Equation 4.

$$K_a/a = (b - [HIn^+])/[HIn^+] \quad (4)$$

If $[HIn^+] \ll b$, $[H^+]$ becomes essentially directly proportional to $[HIn^+]$, as represented by Equation 5.

$$a \propto [HIn^+] \quad (5)$$

In an embodiment, the mass of the indicator dye present on the filter (for example, about 4 ng) is much smaller than the filter mass (for example, about 10 mg) and will not significantly impact the aerosol collection efficiency of the filter.

The filter can be made of any suitable material known in the art. In general, the filter material should be chosen such that the impact on the measurement of the acidity of the aerosol sample can be minimized. For example, the filter can be made of Teflon polymers and glass fibers, neither of which mix with particulate matter or affect the chemical properties of aerosols. Advantageously, the water uptake by a Teflon-impregnated filter is trivial and will not be significantly affected by a change in humidity.

In embodiments where the filter is relocated to a spectrometer, amounts of water in aerosols and the resulting proton concentrations can be affected if the humidity of the air in the spectrometer is appreciably different than that of the air surrounding the filter as the sample passed through. Thus, the humidity of the air in the spectrometer should not be significantly different than that of the air surrounding the filter during collection of the sample.

The proton mass ($Mass_{H^+}$) in nanograms (ng) for a given aerosol sample can be estimated by Equation 6, where $M_{inorg}$ is the inorganic mass in micrograms (µg) and $f_{mass\_H^+}$ is the $H^+$ mass fraction of the total aerosol sample.

$$Mass_{H^+} = 1000 f_{mass\_H^+} M_{inorg} \quad (6)$$

$f_{mass\_H^+}$ can be estimated using known thermodynamic models (Nenes et al., *ISORROPIA: A New Thermodynamic Equilibrium Model for Multiphase Multicomponent Inorganic Aerosols, Aquatic Geochemistry* 4, 1998, 123:152). $M_{inorg}$ can be calculated using Equation 7, where $V_{inorg\_seed}$ is the volumetric concentration of the aerosol sample (which can be obtained, for example, from SMPS data), Q is the volumetric air flow through of the sample, $t_s$ is the sampling duration, and $d_{inorg\_seed}$ is the density of the aerosol sample.

$$M_{inorg} = d_{inorg\_seed} V_{inorg\_seed} Q t_s \quad (7)$$

The density can be calculated using known methods (Semmler et al., *Densities of liquid $H^+/NH_4^+/SO_4^{2-}/NO_3^-/H_2O$ Solutions at Tropospheric Temperatures, Atmos. Environ.* 40, 2006, 467:483).

The color of the filter impregnated with the indicator dye can change color as the filter is exposed to an acidic aerosol sample. For example, if the indicator dye is metanil yellow, the filter may change color from yellow to reddish violet. Such color changes, which can correspond to protons sampled on the filter, can be monitored using a reflectance UV-visible spectrometer.

In an embodiment, an external calibration curve can be obtained using the UV-visible spectrometer data. The available protons in an aerosol sample can be estimated using the correlation between $Mass_{H^+}$ and the absorbance at $\lambda=420$ nm ($Abs_{\lambda=420}$) and $\lambda=545$ nm ($Abs_{\lambda=545}$). An external calibration curve can be obtained from Equations 3 and 5, using Equation 6 to estimate $Mass_{H^+}$. Based on the Lambert-Beer Law, [In] is directly proportional to $Abs_{\lambda=420,In}$ (absorbance of In at $\lambda=420$) and [$HIn^+$] is proportional to $Abs_{\lambda=545,HIn+}$ (absorbance of $HIn^+$ at $\lambda=545$). When $Mass_{H^+}$ is relatively high, Equation 3 can be written as Equation 8, where $c_1$ is the coefficient of proportionality.

$$Mass_{H^+} = c_1 Abs_{\lambda=545,HIn+}/Abs_{\lambda=420,In} \quad (8)$$

When $Mass_{H^+}$ is relatively low, Equation 5 can be rewritten as Equation 9, where $c_2$ is the coefficient of proportionality.

$$Mass_{H^+} = c_2 Abs_{\lambda=545,HIn+} \quad (9)$$

The effect form the UV-Visible spectrum of the indicator dye on the $Abs_{\lambda=545,HIn+}$ is negligible, so it can be assumed that $Abs_{\lambda=545} \approx Abs_{\lambda=545,HIn+}$. The impact of [$HIn^+$] on $Abs_{\lambda=420,In}$ is somewhat larger than those of [In] on $Abs_{\lambda=545,HIn+}$, particularly when [$HIn^+$] is high. However, the effect of [$HIn^+$] onto $Abs_{\lambda=420}$ is still trivial compared to the relative magnitude of $Abs_{\lambda=420,In}$ for aerosol samples with weak to medium $Mass_{H^+}$.

Reflectance UV-Visible spectra can be decoupled into $Abs_{\lambda=420,In}$ by indicator dye only and $Abs_{\lambda=545,HIn+}$ by protonated indicator dye only using least-squares curve fitting. The fitting parameters can include, for example, the center frequency (v), the peak absorbance (A), and the half width at half-height (HWHH). Band shapes in the UV-Visible absorbance spectra can be approximated by a Gaussian mode (Jang et al., *Atmospheric Secondary Aerosol Formation by Heterogeneous Reactions of Aldehydes in the Presence of a Sulfuric Acid Aerosol Catalyst*, Environ. Sci. Technol. 35, 2001, 4758: 4766).

In certain embodiments, the experimentally observed proton mass ($Mass_{H^+,colorimetry}$) of an aerosol sample collected on the filter can be determined from the calibration curve and the absorbance at 545 nm monitored by a reflectance UV-Visible spectrometer using Equation 10.

$$Mass_{H^+,colorimetry} = 99.3 Abs_{\lambda=545,HIn+} \quad (10)$$

$Mass_{H^+,composition}$, a theoretical proton mass estimated from the composition of the aerosol sample, can be calculated using Equation 11, where $M_{inorg}$ is estimated using Equation 7.

$$Mass_{H^+,composition} = 1000 f_{inorg} f_{mass\_H^+} M_{inorg} \quad (11)$$

The proton concentration [$H^+$] (ng/µg) can be obtained by dividing $Mass_{H^+}$ by the inorganic mass ($f_{inorg} M_{inorg}$) of the aerosol sample collected on the filter.

The methods of the present invention are sensitive with a low detection limit of about 0.15 ng for the proton mass of the sample on the filter. The method used for this study is simple and economical because it does not require any workup procedure after particle collection on a filter. Once the optimal range of proton concentrations covered by a calibration curve is set for a type of indicator dye (for example, metanil yellow), a type of a filter, and the concentration of dye solution, the colorimetric analysis of embodiments of the present invention can be used to measure the proton concentration in the aerosol sample.

The terms "passing through," "passed through," or "pass through," as used herein, refer to coming into contact with, being collected on, or passing through.

The term "impregnated with," as used herein, refers to comprising or containing. The embodiments described herein illustrate adaptations of the methods and compositions of the invention. Nonetheless, from the description of these embodiments, other aspects of the invention can also be made and/or practiced.

EXEMPLIFIED EMBODIMENTS

The invention includes, but is not limited to, the following embodiments:

Embodiment 1. A method for measuring the acidity of airborne matter, comprising:
  passing a sample through a filter impregnated with an indicator dye; and
  analyzing the filter using UV-visible spectrometry.

Embodiment 2. The method according to embodiment 1, wherein the indicator dye is metanil yellow.

Embodiment 3. The method according to any of embodiments 1-2, wherein the filter comprises Teflon polymers and glass fibers.

Embodiment 4. The method according to any of embodiments 1-3, further comprising obtaining a calibration curve using previous samples.

Embodiment 5. The method according to any of embodiments 1-4, wherein the sample is an aerosol sample.

Embodiment 6. The method according to any of embodiments 1-5, further comprising passing the sample through a cartridge to remove ammonia, a cartridge to remove nitric acid gas, or both, before passing the sample through the filter.

Embodiment 7. The method according to any of embodiments 1-6, further comprising relocating the filter to a spectrometer before analyzing the filter using UV-visible spectrometry.

Embodiment 8. The method according to any of embodiments 1-7, wherein the sample is passed through the filter for a period of time of from about 20 seconds to about 120 seconds.

Embodiment 9. A device for measuring the acidity of airborne matter, comprising:
a filter impregnated with an indicator dye; and
a UV-visible spectrometer.

Embodiment 10. The device according to embodiment 9, wherein the indicator dye is metanil yellow.

Embodiment 11. The device according to any of embodiments 9-10, wherein the filter comprises Teflon polymers and glass fibers.

Embodiment 12. The device according to any of embodiments 9-11, further comprising a cartridge to remove ammonia, a cartridge to remove nitric acid gas, or both.

Embodiment 13. The device according to any of embodiments 9-12, further comprising a detector chamber, wherein the filter can be located in the detector chamber or the UV-visible spectrometer.

Embodiment 14. The device according to any of embodiments 9-13, wherein the device is capable of measuring the acidity of a sample of airborne matter in a period of time of from about 20 seconds to about 120 seconds.

Materials and Methods

A 13 mm diameter sampling filter (Borosilicate microfibers reinforced with woven glass cloth and bonded with Teflon, Gelman Science Palflex, Type: TX40H120-WW,) was dyed with an 0.02% aqueous solution of metanil yellow (Aldrich) for 10 minutes. Metanil yellow was used in low concentration so that it exerted essentially no control on proton concentrations of the aerosol on the filter. The dyed filters were dried by gentle streams of nitrogen or clean air, and kept in a tightly sealed bottle to avoid contact with ambient air until used for aerosol sampling. No mass change, determined by weighing the dried filter mass before and after dyeing with metanil yellow, appeared within the error range of the balance.

An aerosol sample for colorimetric analysis was collected from the Teflon chamber on a filter dyed with metanil yellow using a pump (Gast, DOA-P704-AA) at 13 L/min. The sampling filters were weighed (MX5 Mettler-Toledo Ltd., England) before and after sampling to estimate the aerosol mass collected on the filter. Both SMPS data and the aerosol mass measurements were used to estimate proton concentrations. The mass change by the gas adsorption onto the small size of the filter, tested using two (front and back) 13 mm filters, was negligible.

The color changes of a filter sample associated with proton concentrations were monitored by reflectance UV-visible spectroscopy (UV-3600, Shmadzu, Kyoto, Japan) measuring a wavelength range of 300 nm to 800 nm. The integrating sphere attachment (ISR-3100) was used to measure the spectra in the reflectance mode. The photomultiplier (PMT) covered from 300 nm to 700 nm, and the Indium/Gallium/Arsenide (InGaAs) photodiode detector from 700 nm to 800 nm. The sampling interval was 1 nm and the slit width was 2.0 nm. Packed barium sulfate was used for reference and baseline. The temperature for the instrumentation ranged from about 295° C. to about 298° C., and the relative humidity ranged from about 40% to about 45%.

All experiments were conducted in a 2 $m^3$ indoor Teflon film chamber without photoirradiation (Czoschke et al., *Acidity Effects on the Formation of α-pinene Ozone SOA in the Presence of Inorganic Seed, Atmos. Environ* 40, 2006, 4370:4380; Jang et al., *SOA Formation from Partitioning and Heterogeneous Reactions: Model Study in the Presence of Inorganic Species, Environ. Sci. & Technol.* 40, 2006, 3013:3022; Northcross et al., *Increases in Heterogeneous SOA Yield from Ozonolysis of Monoterpenes, Atmos Environ.* 41, 2007, 1483:1493). The chamber was flushed with clean air from two clean air generators (Aadco Model 737, Rockville, Md.; Whatman Model 75-52, Haverhill, Mass.) prior to each experiment. The ammonia concentration in the chamber bath air created from clean air generators was negligible. A seed aerosol was injected into the chamber using an atomizer (TSI, Model 3076, Shoreview, Minn.). Inorganic seed aerosols were made from an aqueous solution (0.01 M) of ammonium sulfate [$(NH_4)_2SO_4$, AS], ammonium hydrogen sulfate ($NH_4HSO_4$, AHS), and sulfuric acid ($H_2SO_4$). After injecting seed aerosols, ozone was injected into the chamber by passing clean air through a photolytic ozone generator (Jelight Model 600, Irvine, Calif.). The ozone was monitored using a photometric ozone detector (Thermo Environmental Instruments, Model 49). An excess of ozone was injected to achieve an α-pinene limited experiment. α-Pinene (Aldrich, 98%) as a 20% solution in carbon tetrachloride (99.9%, Aldrich) was introduced into the chamber by passing the clean air through a T-shaped glass tube that was gently heated using a heat gun.

The particle population was measured using a scanning mobility particle sizer (TSI, SMPS Model 3080 Shoreview, Minn.) associated with a condensation nuclei counter (TSI, Model 3025A). The particle number concentration was corrected for particle loss to the wall using a semi-empirical exponential decay function for each particle diameter over time (McMurry et al., *Gas and Aerosol Wall Losses in Teflon Film Smog Chambers, Environ. Sci. Technol.* 19, 1985, 1176:82). Temperature and humidity were measured with an electronic thermo-hygrometer (Hanna Instruments, Italy). The temperatures for the experiments were from about 294° C. to about 297° C.

EXAMPLES

Example 1

Experiments to Produce an External Calibration Curve

Nineteen samples were collected and analyzed, one at a time. Each sample passed through a cartridge to remove ammonia, a cartridge to remove nitric acid gas, and then a filter impregnated with an indicator dye. The filter was made of Teflon polymers and glass fibers, and the indicator dye was metanil yellow. The experimental conditions and the resulting data to produce the external calibration curve are shown in Table 1.

TABLE 1

Indoor Teflon Film Chamber Experiments of Inorganic Seed Aerosol Known for Compositions

| Sample # | $F_{SA}$ | sample time (sec) | volumetric concentration ($nm^3/m^3$) | $M_{inorg}$ (μg) | density (g/mL) | $Abs_{\lambda=545}$ | $Abs_{\lambda=420, In}$ | $Abs_{\lambda=545, Hin+}$ | $Mass_{H+}$ (ng) |
|---|---|---|---|---|---|---|---|---|---|
| S1 | 0.67 | 120 | 9.65E+11 | 35.13 | 1.4 | 0.2928 | 0.0385 | 0.291 | 107 |
| S2 | 0.67 | 60 | 8.61E+11 | 15.67 | 1.4 | 0.3262 | 0.0817 | 0.308 | 48 |
| S3 | 0.67 | 40 | 8.30E+11 | 10.07 | 1.4 | 0.2773 | 0.1551 | 0.274 | 31 |
| S4 | 0.67 | 20 | 8.07E+11 | 4.9 | 1.4 | 0.1588 | 0.2288 | 0.156 | 15 |
| S5 | 0.67 | 120 | 2.27E+11 | 8.26 | 1.4 | 0.2688 | 0.1665 | 0.256 | 25 |

TABLE 1-continued Indoor Teflon Film Chamber Experiments of Inorganic Seed Aerosol Known for Compositions

| Sample # | $F_{SA}$ | sample time (sec) | volumetric concentration ($nm^3/m^3$) | $M_{inorg}$ (µg) | density (g/mL) | $Abs_{\lambda=545}$ | $Abs_{\lambda=420,In}$ | $Abs_{\lambda=545,HIn+}$ | $Mass_{H+}$ (ng) |
|---|---|---|---|---|---|---|---|---|---|
| S6 | 0.67 | 60 | 4.02E+11 | 7.32 | 1.4 | 0.2551 | 0.2104 | 0.249 | 22 |
| S7 | 0.67 | 40 | 4.01E+11 | 4.87 | 1.4 | 0.1834 | 0.256 | 0.175 | 15 |
| S8 | 0.67 | 120 | 2.21E+11 | 8.04 | 1.4 | 0.223 | 0.1982 | 0.203 | 25 |
| S9 | 0.67 | 60 | 2.07E+11 | 3.77 | 1.4 | 0.1206 | 0.2415 | 0.111 | 11 |
| S10 | 0.67 | 35 | 2.08E+11 | 2.21 | 1.4 | 0.0645 | 0.3067 | 0.07 | 7 |
| S11 | 0.67 | 20 | 2.08E+11 | 1.26 | 1.4 | 0.0207 | 0.3238 | 0.025 | 4 |
| S12 | 0.42 | 130 | 3.21E+11 | 10.85 | 1.2 | 0.1344 | 0.2571 | 0.13 | 17 |
| S13 | 0.42 | 60 | 2.85E+11 | 4.45 | 1.2 | 0.0401 | 0.2947 | 0.053 | 7 |
| S14 | 0.36 | 60 | 3.73E+11 | 5.72 | 1.18 | 0.027 | 0.2552 | 0.025 | 7 |
| S15 | 0.36 | 60 | 3.56E+11 | 5.46 | 1.18 | 0.031 | 0.2875 | 0.039 | 7 |
| S16 | 0.33 (AS) | 120 | 2.52E+11 | 7.73 | 1.18 | 0.0022 | 0.2414 | 0.012 | ~0 |
| S17 | 0.33 (AS) | 60 | 2.34E+11 | 3.59 | 1.18 | 0.0005 | 0.2536 | 0.001 | 0 |
| C1 | citric acid | 60 | 3.36E+11 | 7.27 | 1.665 | 0.0079 | 0.2517 | 0.013 | 0.78 |
| C2 | citric acid | 35 | 3.02E+11 | 3.81 | 1.665 | −0.005 | 0.2753 | 0.003 | 0 |

For the experiments detailed in Table 1, $M_{inorg}$ was estimated using Equation 7 with a sampling flow rate of 13 L/min. The density was estimated by known methods (Semmler et al., 2006, supra). The absorbance at 545 nm $(Abs)_{\lambda=545}$ was without curve fitting while $Abs_{\lambda=420,In}$ and $Abs_{\lambda=545,HIn+}$ were with curve fitting. Also, $Mass_{H+}$ was estimated using $M_{inorg}$ and the mass fraction of $H^+$ predicted by a thermodynamic model such as ISORROPIA, except for the $Mass_{H+}$ values for samples C1 and C2, which were obtained using the calibration curve of FIG. 3C (Nenes et al., 1998, supra).

Figure 3A:
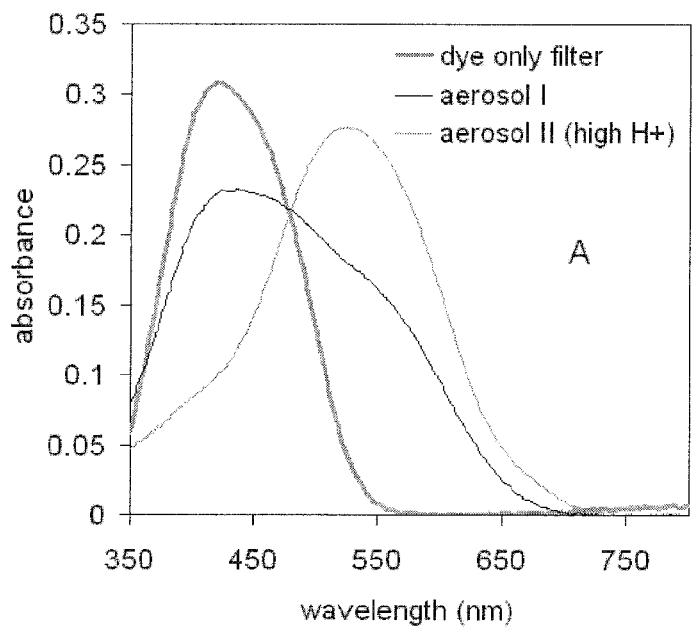
FIG. 3A shows absorbance spectra for a sample of acidic aerosol collected on a filter according to a method of an embodiment of the present invention.
Figure 3B:
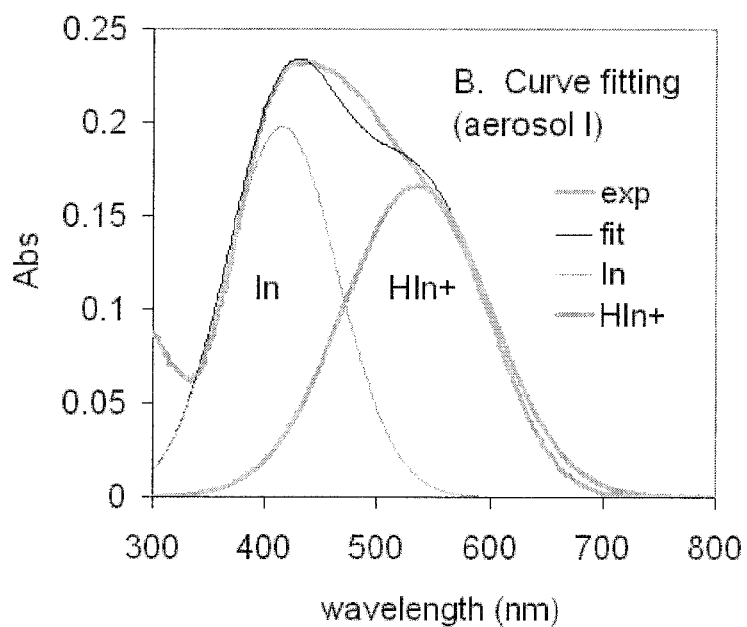
FIG. 3B shows curve fitting absorbance spectra for the aerosol I sample from FIG. 2A.
Figure 4A:
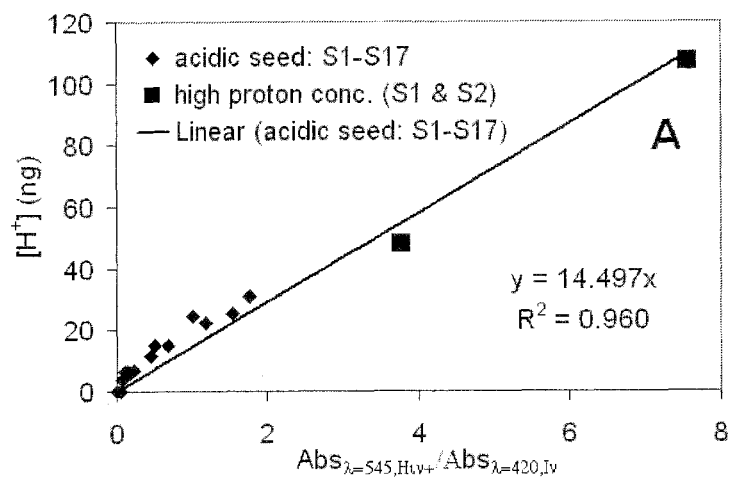
FIGS. 4A-4C show calibration curves for samples used according to an embodiment of the present invention.
Figure 4B:
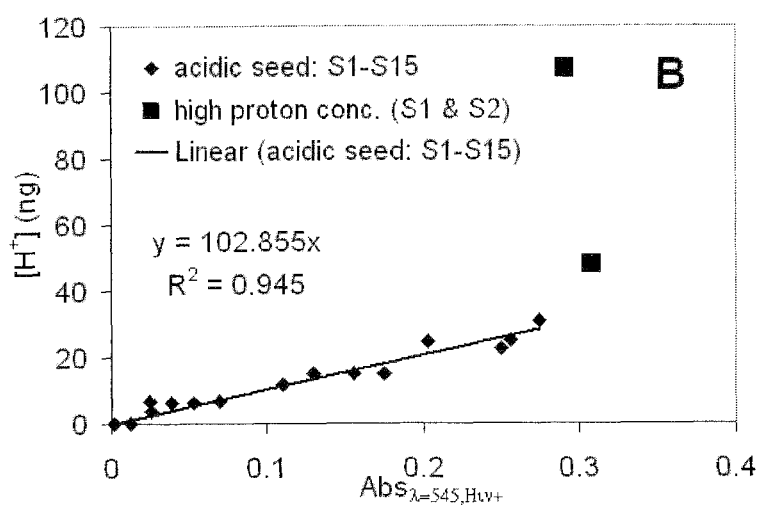
Figure 4C:
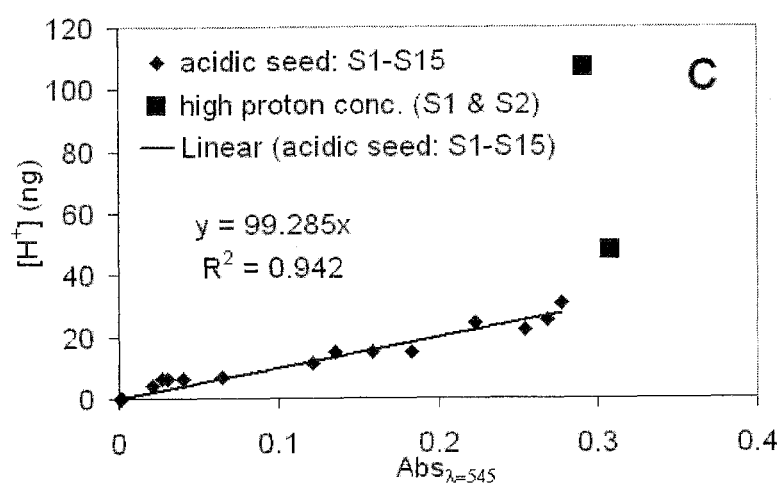

FIG. 3A shows the absorbance spectra for two samples (one with high acidity) and just the filter and dye. FIG. 3B shows the curve-fitting result applied to the aerosol I sample of FIG. 3A. FIG. 4A shows the calibration curve plotting $Mass_{H+}$ vs. $Abs_{\lambda=545,HIn+}/Abs_{\lambda=420,In}$ with slope=14.497 setting the intercept equal to zero. A strong linearity ($R^2$=0.96) including data points S1 and S2 indicates that Equation 8 is appropriate for high $Mass_{H+}$ data. The same data set in Table 1 were applied to Equation 9 to obtain the calibration curves for $Mass_{H+}$ vs. $Abs_{\lambda=545,HIn+}$ with curve fitting (FIG. 4B) as well as $Mass_{H+}$ vs. $Abs_{\lambda=545}$ with no curve fitting (FIG. 4C). Data points S1 and S2 in high $Mass_{H+}$ became outliers in FIGS. 4B and 4C because Equation 9 was originally designed for relative low $Mass_{H+}$. Excluding S1 and S2, the strong linearity is observed in both FIG. 4B ($R^2$=0.945) and FIG. 4C ($R^2$=0.942) using data points S3-S17. More importantly, the slope in FIG. 4B is not statistically different from the slope in FIG. 4C at a confidence level higher than 0.99. This indicate that proton concentrations, if the concentration is not extremely high (e.g., S1 and S2), can be reasonably predicted using the data from the single wavelength at $\lambda=545$ without decoupling of UV spectra into two components associated with [$HIn^+$] and [$In$] of metanil yellow.

Example 2

Experiments for SOA Formation in the Presence of Acidic Inorganic Seed Aerosol

Thirteen samples were collected and analyzed, one at a time. Each sample passed through a cartridge to remove ammonia, a cartridge to remove nitric acid gas, and then a filter impregnated with an indicator dye. The filter was made of Teflon polymers and glass fibers, and the indicator dye was metanil yellow. Table 2 summarizes the experimental conditions applied to SOA formation using an indoor chamber.

TABLE 2

Indoor Teflon Film Chamber Experiments for SOA Formation in the Presence of Acidic Inorganic Seed Aerosol

| Sample # | aerosol | α-P (ppb) | $O_3$ (ppb) | % RH | sample time (sec) | volumetric concentration ($nm^3/m^3$) | $f_{inorg}$ | $M_{inorg}$ (µg) | $Abs_{\lambda=545}$ | $Mass_{H+}$, colorimetry (ng) | $Mass_{H+}$, composition (ng) | $f_{os}$ |
|---|---|---|---|---|---|---|---|---|---|---|---|---|
| h1 | SOA/seed | 260 | 150 | 40-45 | 60 | 7.29E+11 | 0.94 | 12.47 | 0.225 | 22.2 | 35.2 | 0.36 |
| h2 | SOA/seed | | | 40-45 | 60 | 6.17E+11 | 0.84 | 9.43 | 0.167 | 12.2 | 26.6 | 0.37 |
| a1 | SOA/seed | 375 | 540 | 40-45 | 120 | 4.99E+11 | 0.57 | 10.35 | 0.133 | 9.1 | 29.2 | 0.55 |
| a2 | SOA/seed | | | 40-45 | 120 | 5.61E+11 | 0.41 | 8.37 | 0.079 | 4.6 | 23.6 | 0.67 |
| a3 | SOA/seed | | | 40-45 | 120 | 6.48E+11 | 0.27 | 6.37 | 0.038 | 2.7 | 18.0 | 0.80 |
| b1 | seed | 150 | 303 | 30 | 30 | 3.34E+11 | 1 | 2.49 | 0.124 | 12.4 | 12.6 | n.a. |
| b2 | SOA/seed | | | 30 | 30 | 3.44E+11 | 0.87 | 2.25 | 0.104 | 10.3 | 11.4 | 0.17 |
| b3 | SOA/seed | | | 30 | 30 | 4.53E+11 | 0.63 | 2.13 | 0.073 | 7.3 | 10.8 | 0.41 |
| b4 | SOA/seed | | | 30 | 30 | 5.75E+11 | 0.44 | 1.88 | 0.08 | 7.9 | 9.5 | 0.36 |
| c1 | seed | 150 | 248 | 33 | 30 | 2.89E+11 | 1 | 2.52 | 0.117 | 11.6 | 12.0 | n.a. |
| c2 | SOA/seed | | | 33 | 30 | 3.02E+11 | 0.92 | 2.09 | 0.091 | 9.1 | 10.6 | 0.21 |
| c3 | SOA/seed | | | 33 | 30 | 4.64E+11 | 0.54 | 1.90 | 0.072 | 7.1 | 9.6 | 0.39 |
| c4 | SOA/seed | | | 33 | 30 | 4.85E+11 | 0.49 | 1.80 | 0.071 | 7.1 | 9.1 | 0.39 |

For the experiments detailed in Table 2, α-P is the initial α-pinene concentration, $O_3$ is the initial ozone concentration, and $f_{inorg}$ is the inorganic seed fraction of the total aerosol sample. $M_{inorg}$ was estimated using Equation 7 with a sampling flow rate of 13 L/min. The density of both inorganic and organic components was 1.4 g/mL. $Mass_{H+,colorimetry}$ is the proton concentration estimated using the calibration curve of FIG. 3C, and the error for $Mass_{H+,colorimetry}$ was about 13% on average. The associated error for $Mass_{H+,colorimetry}$ was about 10% on average. The conversion fraction of sulfuric acid to organic sulfate ($f_{os}$) was obtained using Equation 12.

Figure 5A:
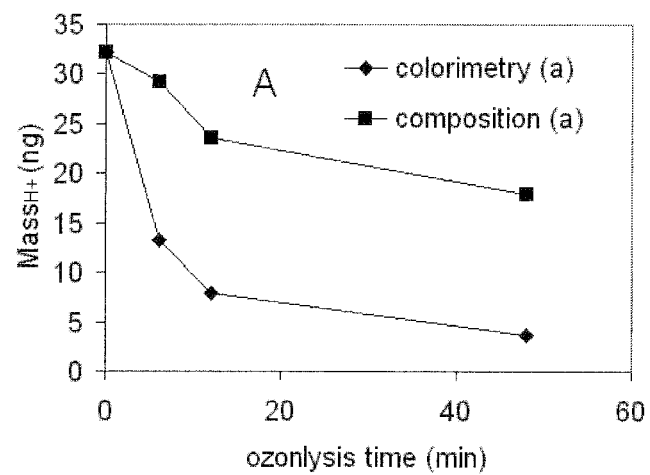
FIGS. 5A-5C show time profiles for samples used according to an embodiment of the present invention.
Figure 5B:
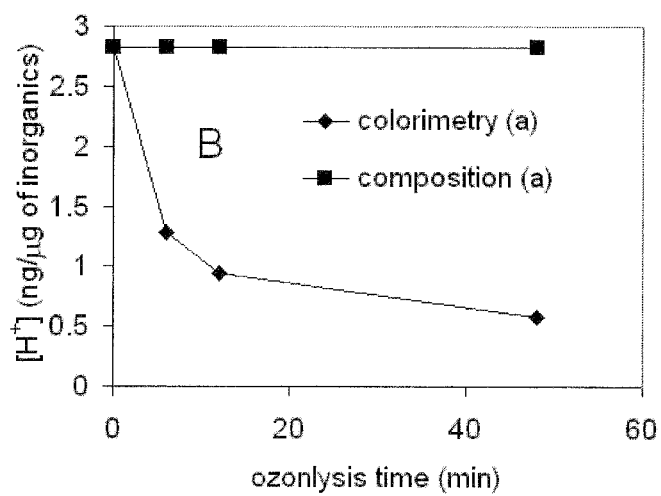
Figure 5C:
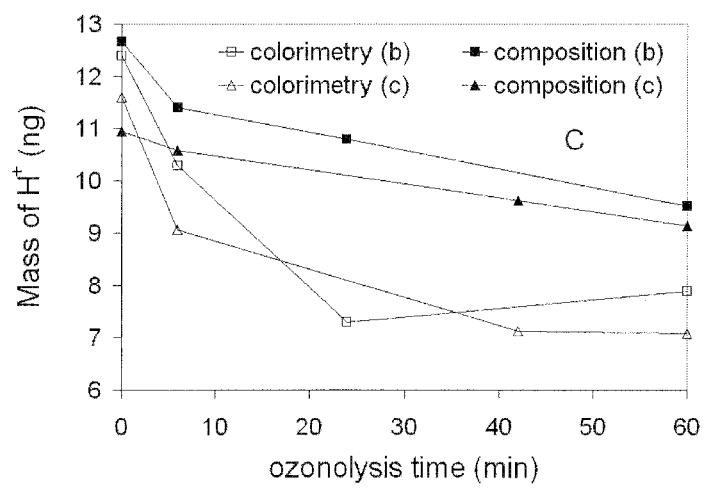
Figure 6:
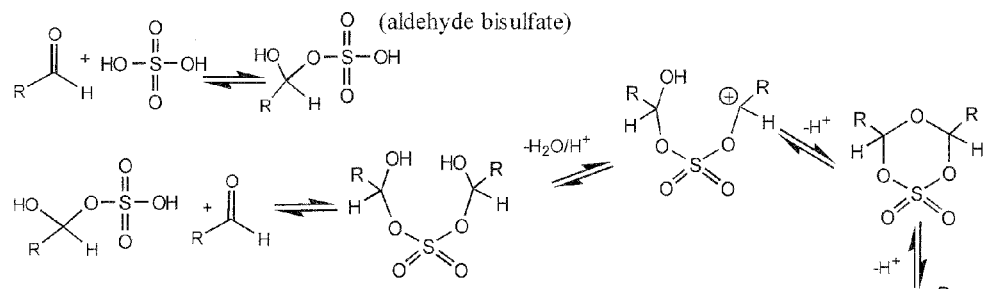
FIG. 6 shows proposed mechanisms for the formation of organic sulfate by the reaction of sulfuric acid with organic carbonyls.
Figure 6:
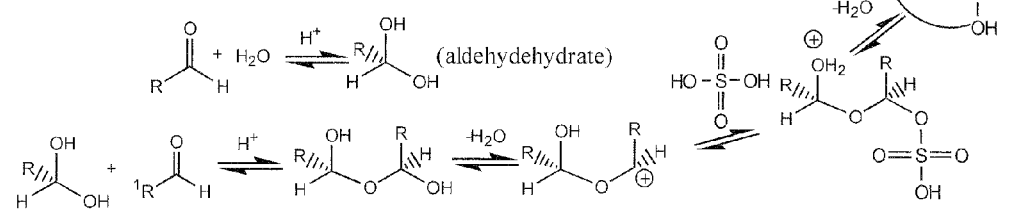
Figure 6:
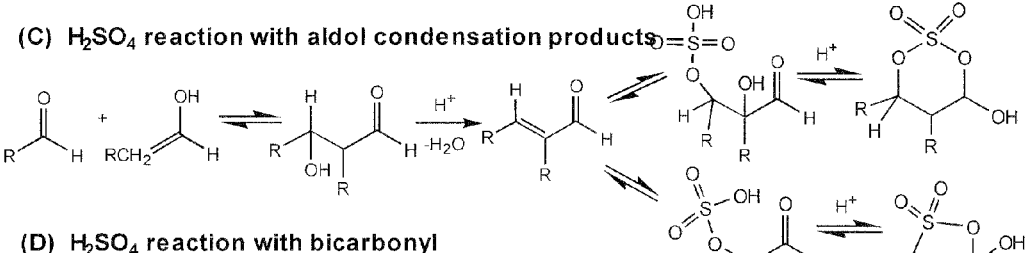
Figure 6:
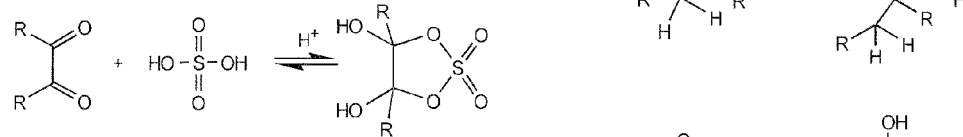
Figure 6:
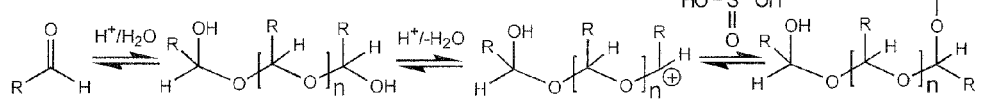

FIG. 5A shows $Mass_{H^+,colorimetry}$ and $Mass_{H^+,composition}$ for the a-series samples. FIG. 5B shows the observed and estimated [$H^+$] for the a-series samples. FIG. 5C shows the $Mass_{H^+,colorimetry}$ and $Mass_{H^+,composition}$ for b- and c-series SOA data. Overall, $Mass_{H^+,composition}$ is higher than observed $Mass_{H^+,colorimetry}$. More importantly, the gap between $Mass_{H^+,colorimetry}$ and $Mass_{H^+,composition}$ becomes greater as the acidic inorganic aerosol is coated with SOA. A possible explanation for this observation is transformation of sulfuric acid into organic sulfates by the reaction of $H_2SO_4$ with organic species in aerosol (Liggio et al., *Heterogeneous Reactions of Glyoxal on Particulate Matter: Identification of Acetals and Sulfate Esters, Environ. Sci. Technol.* 39, 2005, 1532:1541; Surratt et al., *Evidence for Organosulfates in Secondary Organic Aerosol, Environ. Sci. Technol.* 41, 2007, 517:527). The formation of organic sulfates in aerosols may be very complex due to cross reactions of organic sulfates with other products from heterogeneous acid-catalyzed reactions. FIG. 6 shows some possible mechanisms for the formation of organic sulfates linked to other heterogeneous acid-catalyzed reactions in acidic aerosol. The possible reaction mechanisms include organic bisulfate formation (reaction A), a trioxane-type reaction (reactions A and B) with two molecules of aldehydes and one molecule of $H_2SO_4$, addition of $H_2SO_4$ to alkenes (reaction C), sulfate ester formation (reaction D) with bicarbonyls (Liggio et al., 2005, supra), and $H_2SO_4$ reactions of oligomers (reaction E).

The fraction of conversion of sulfuric acid to organic sulfate ($f_{os}$) can be estimated by Equation 12.

$$f_{os} = (Mass_{H^+,composition} - Mass_{H^+,colorimetry}) / Mass_{H^+,composition} \quad (12)$$

Table 2 also shows estimated $f_{os}$ values for the samples. As shown in Table 1 and Table 2, the sampling time necessary to monitor color changes associated with aerosol acidity can range from about 20 seconds to about 120 seconds.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A device for measuring the acidity of airborne matter, comprising:
    a filter impregnated with an indicator dye;
    a UV-visible spectrometer;
    a cartridge to remove ammonia; and
    a cartridge to remove nitric acid gas,
    wherein the filter comprises Teflon polymers and glass fibers.

2. The device according to claim 1, wherein the indicator dye is metanil yellow.

3. The device according to claim 1, further comprising a detector chamber, wherein the filter can be located in the detector chamber or the UV-visible spectrometer.

4. The device according to claim 1, wherein the device is capable of measuring the acidity of a sample of airborne matter in a period of time of from about 20 seconds to about 120 seconds.

* * * * *